US00PP28654P3

(12) United States Plant Patent
van Sambeek

(10) Patent No.: US PP28,654 P3
(45) Date of Patent: Nov. 14, 2017

(54) ***SALVIA* PLANT NAMED 'BAREULBECILAS'**

(50) Latin Name: *Salvia nemorosa*
Varietal Denomination: Bareulbecilas

(71) Applicant: Ellen van Sambeek, Aalsmeer (NL)

(72) Inventor: Ellen van Sambeek, Aalsmeer (NL)

(73) Assignee: Dümmen Group B.V., De Lier (NL)

( * ) Notice: Subject to any disclaimer, the term of this patent is extended or adjusted under 35 U.S.C. 154(b) by 60 days.

(21) Appl. No.: 14/756,928

(22) Filed: Oct. 30, 2015

(65) Prior Publication Data

US 2017/0127601 P1 May 4, 2017

(51) Int. Cl.
*A01H 5/02* (2006.01)

(52) U.S. Cl.
USPC ..... Plt./475

(58) Field of Classification Search
USPC ..... Plt./475
See application file for complete search history.

*Primary Examiner* — June Hwu
(74) *Attorney, Agent, or Firm* — C. A. Whealy

(57) ABSTRACT

A new and distinct cultivar of *Salvia* plant named 'Bareulbecilas', characterized by its upright and compact plant habit; vigorous growth habit; freely branching habit; early and freely flowering habit; upright inflorescences with light blue-colored flowers; and good garden performance.

1 Drawing Sheet

Botanical designation: *Salvia nemorosa.*
Cultivar denomination: 'BAREULBECILAS'.

BACKGROUND OF THE INVENTION

The present invention relates to a new and distinct cultivar of *Salvia* plant, botanically known as *Salvia nemorosa* and hereinafter referred to by the name 'Bareulbecilas'.

The new *Salvia* plant is a product of a planned breeding program conducted by the Inventor in Aalsmeer, The Netherlands. The objective of the breeding program is to create new compact *Salvia* plants with unique and attractive flowers.

The new *Salvia* plant originated from a cross-pollination in June, 2013 of a proprietary selection of *Salvia nemorosa* identified as code number SV-0001, not patented, as the female, or seed, parent with a proprietary selection of *Salvia nemorosa* identified as code number SV-0005, not patented, as the male, or pollen, parent. The new *Salvia* plant was discovered and selected by the Inventor as a single flowering plant from within the progeny of the stated cross-pollination in a controlled environment in Aalsmeer, The Netherlands in December, 2013.

Asexual reproduction of the new cultivar by vegetative terminal cuttings in Aalsmeer, The Netherlands, since December, 2013 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Bareulbecilas'. These characteristics in combination distinguish 'Bareulbecilas' as a new and distinct *Salvia* plant:

1. Upright and compact plant habit.
2. Vigorous growth habit.
3. Freely branching habit.
4. Early and freely flowering habit.
5. Upright inflorescences with light blue-colored flowers.
6. Good garden performance.

Plants of the new *Salvia* can be compared to plants of the female parent selection. Plants of the new *Salvia* differ primarily from plants of the female parent selection in flower bud and flower color as plants of the female parent selection have red-colored flower buds and dark blue-colored flowers.

Plants of the new *Salvia* can be compared to plants of the male parent selection. Plants of the new *Salvia* differ primarily from plants of the male parent selection in the following characteristics:

1. Plants of the new *Salvia* are more compact than and not as broad as plants of the male parent selection.
2. Plants of the new *Salvia* and the male parent selection differ in flower color as plants of the male parent selection have pink-colored flowers.
3. Flowers of plants of the new *Salvia* produce little to no pollen whereas flowers of plants of the male parent selection produce pollen.

Plants of the new *Salvia* can be compared to plants of *Salvia nemorosa* 'May Night', not patented. In side-by-side comparisons conducted in Aalsmeer, The Netherlands, plants of the new *Salvia* differed from plants of 'May Night' in the following characteristics:

1. Plants of the new *Salvia* were more compact in plant habit than plants of 'May Night'.
2. Plants of the new *Salvia* had shorter internodes than plants of 'May Night'.
3. Plants of the new *Salvia* were more freely branching than plants of 'May Night'.
4. Plants of the new *Salvia* had smaller leaves than plants of 'May Night'.

5. Plants of the new *Salvia* had smaller flowers than plants of 'May Night'.
6. Plants of the new *Salvia* and 'May Night' differed in flower color as plants of 'May Night' had dark blue-colored flowers.

BRIEF DESCRIPTION OF THE PHOTOGRAPH

The accompanying colored photograph illustrates the overall appearance of the new *Salvia* plant showing the colors as true as it is reasonably possible to obtain in colored reproductions of this type. Colors in the photograph may differ slightly from the color values cited in the detailed botanical description which accurately describe the actual colors of the new *Salvia* plant. The photograph is a side perspective view of a typical flowering plant of 'Bareulbecilas' grown in a container.

DETAILED BOTANICAL DESCRIPTION

The aforementioned photograph and following observations, measurements and values describe plants grown during the summer in 13-cm containers in a glass-covered greenhouse in Aalsmeer, The Netherlands and under cultural practices typical of commercial *Salvia* production. During the production of the plants, day temperatures averaged 22° C. and night temperatures averaged 17° C. Plants were pinched one time and were three months old when the photograph was taken and two months old when the description was taken. In the detailed description, color references are made to The Royal Horticultural Society Colour Chart, 2007 Edition, except where general terms of ordinary dictionary significance are used.

Botanical classification: *Salvia nemorosa* 'Bareulbecilas'.

Parentage:

*Female, or seed, parent*.—Proprietary selection of *Salvia nemorosa* identified as code number SV-0001, not patented.

*Male, or pollen, parent*.—Proprietary selection of *Salvia nemorosa* identified as code number SV-0005, not patented.

Propagation:

*Type*.—By vegetative terminal cuttings.

*Time to initiate roots, summer*.—About ten days at temperatures about 26° C.

*Time to initiate roots, winter*.—About two weeks at temperatures about 23° C.

*Time to produce a rooted young plant, summer*.—About twelve days at temperatures about 23° C.

*Time to produce a rooted young plant, winter*.—About 16 days at temperatures about 18° C.

*Root description*.—Medium in thickness, fibrous; typically white to light yellow in color, actual color of the roots is dependent on substrate composition, water quality, fertilizer type and formulation, substrate temperature and physiological age of roots.

*Rooting habit*.—Moderately freely branching; dense.

Plant description:

*Plant and growth habit*.—Herbaceous perennial typically grown as a container and garden plant; upright and compact plant habit; uniform and vigorous growth habit; rapid growth rate.

*Branching habit*.—Freely basal branching with about six primary lateral branches per plant.

*Plant height*.—About 35 cm.

*Plant width*.—About 30 cm.

*Lateral branch description*.—Length: About 30 cm. Diameter: About 8 mm. Internode length: About 5 cm. Strength: Moderately strong. Aspect: Mostly upright. Texture: Pubescent. Color: Close to 138A.

Leaf description:

*Arrangement*.—Opposite, simple.

*Length*.—About 5 cm.

*Width*.—About 2 cm.

*Shape*.—Elliptical.

*Apex*.—Acute.

*Base*.—Cordate.

*Margin*.—Crenate.

*Texture, upper surface*.—Rugose, glabrous.

*Texture, lower surface*.—Smooth, glabrous.

*Venation pattern*.—Pinnate, arcuate.

*Color*.—Developing leaves, upper surface: Close to 137B. Developing leaves, lower surface: Close to 137D. Fully expanded leaves, upper surface: Close to 137B; venation, close to 148C. Fully expanded leaves, lower surface: Close to 137C; venation, close to 148D.

*Petioles*.—Length: About 1 cm. Diameter: About 2 mm. Texture, upper and lower surfaces: Sparsely pubescent. Color, upper surface: Close to 147C. Color, lower surface: Close to 148C.

Flower description:

*Flower arrangement and shape*.—Single bilabiate and sessile flowers arranged on erect spikes; freely flowering habit with about 81 flowers developing per inflorescence and about 1,500 flowers developing per plant during the flowering season; flowers face mostly outwardly; flowers not persistent.

*Fragrance*.—None detected.

*Natural flowering season*.—Early flowering habit, plants begin flowering about three weeks after planting; plants flower during June and July in an outdoor environment in The Netherlands.

*Flower buds*.—Length: About 1.5 cm. Diameter: About 7 mm. Shape: Conical. Color: Close to 138C.

*Inflorescence height*.—About 10 cm.

*Inflorescence diameter*.—About 2 cm.

*Flower diameter*.—About 5 mm.

*Flower height*.—About 1 cm.

*Flower throat diameter*.—About 3 mm.

*Flower tube length*.—About 6 mm.

*Flower tube diameter, proximally*.—About 3 mm.

*Petals*.—Arrangement: Five petals fused at the base forming a single upper banner petal (upper lip), two lateral petals and two lower petals (broad lower lip). Upper and lower lip length: About 1 cm. Upper and lower lip width: About 7 mm. Upper and lower lip shape: Round. Upper and lower lip apex: Round. Upper and lower lip base: Fused into a narrow tube. Upper and lower lip margin: Entire. Upper and lower lip texture, upper surface: Smooth, glabrous. Upper and lower lip texture, lower surface: Pubescent. Texture, throat: Smooth, glabrous. Texture, tube: Smooth, glabrous. Color: Upper and lower lip, when opening, upper and lower surfaces: Close to 92B. Upper and lower lip, fully opened, upper surface: Close to 92C; venation, close to 93B; color does not fade with development. Upper and lower lip, fully opened, lower surface: Close to 92C; venation, close to 92C; color does not fade with development.

Throat: Close to 91D; venation, close to 91D. Tube: Close to 91D; venation, close to 91D.

*Calyx*.—Arrangement: Five sepals fused to form a campanulate calyx. Length: About 5 mm. Width: About 2 mm. Shape: Deltoid. Apex: Acuminate. Margin: Entire. Texture, inner and outer surfaces: Smooth, glabrous. Color, inner surface: Close to 147B. Color, outer surface: Close to 143C.

*Peduncles*.—Length: About 5 cm. Diameter: About 2 mm. Strength: Strong. Aspect: Mostly erect; laterals, about 30° from vertical. Texture: Smooth, glabrous. Color: Close to 147C.

*Reproductive organs*.—Stamens: Quantity per flower: Two. Filament length: About 1 mm. Filament color: Close to 91D. Anther shape: Oblique. Anther length: About 0.5 mm. Anther color: Close to 162B. Pollen amount: Little to none. Pollen color: Close to 162B. Pistils: Quantity per flower: One. Pistil length: About 1 cm. Stigma shape: Bi-lobed. Stigma color: Close to 92A. Style length: About 9 mm. Style color: Close to 91D. Ovary color: Close to 91D.

*Seeds and fruits*.—Seed and fruit production has not been observed on plants of the new *Salvia*.

Disease & pest resistance: Plants of the new *Salvia* have not been noted to be resistant to pathogens and pests common to *Salvia* plants.

Garden performance: Plants of the new *Salvia* have exhibited good garden performance and to be tolerant to rain, wind and temperatures ranging from about −20° C. to about 30° C.

It is claimed:

1. A new and distinct *Salvia* plant named 'Bareulbecilas' as illustrated and described.

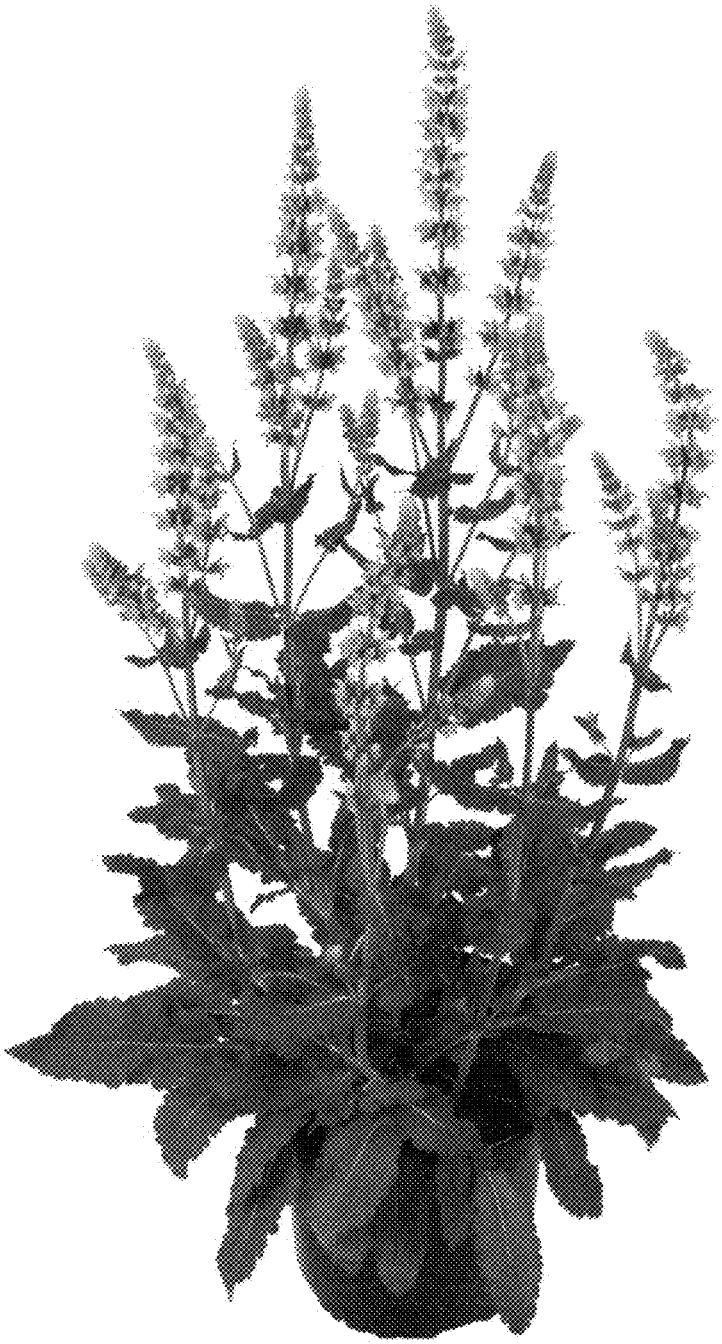

* * * * *